US010428324B1

(12) United States Patent
Coons et al.

(10) Patent No.: US 10,428,324 B1
(45) Date of Patent: Oct. 1, 2019

(54) ACOUSTIC MANIPULATION OF FLUIDS BASED ON EIGENFREQUENCY

(71) Applicant: Los Alamos National Security, LLC, Los Alamos, NM (US)

(72) Inventors: James E. Coons, Los Alamos, NM (US); James A. Ten Cate, Los Alamos, NM (US); Eric Y. Raby, Los Alamos, NM (US); Daniel M. Kalb, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 72 days.

(21) Appl. No.: 15/400,890

(22) Filed: Jan. 6, 2017

Related U.S. Application Data

(60) Provisional application No. 62/276,755, filed on Jan. 8, 2016.

(51) Int. Cl.
*C12N 13/00* (2006.01)
*H03H 9/17* (2006.01)
*H03H 9/13* (2006.01)
*H01L 41/187* (2006.01)
*B01D 21/28* (2006.01)
*C02F 1/36* (2006.01)
*C12N 1/12* (2006.01)
*C12M 1/00* (2006.01)
*C12M 1/34* (2006.01)
*C12M 1/36* (2006.01)
*C02F 101/30* (2006.01)

(52) U.S. Cl.
CPC .......... *C12N 13/00* (2013.01); *B01D 21/283* (2013.01); *C02F 1/36* (2013.01); *C12M 41/42* (2013.01); *C12M 41/48* (2013.01); *C12M 47/02* (2013.01); *C12N 1/12* (2013.01); *H01L 41/1876* (2013.01); *H03H 9/13* (2013.01); *H03H 9/176* (2013.01); *C02F 2101/30* (2013.01)

(58) Field of Classification Search
CPC ......... B06B 3/00; C11B 1/106; B01D 21/283; B01D 43/00; B01J 19/10; G10K 11/04; G06F 17/5018; G06F 2217/16; G06F 17/5009; G06F 2217/08; G06F 8/34; G01N 2291/0256; G01N 2291/0257; G01N 29/036; G01N 33/54373; Y10T 436/11; G16C 20/10; G16C 99/00
See application file for complete search history.

(56) References Cited

U.S. PATENT DOCUMENTS

| | | | | |
|---|---|---|---|---|
| 5,164,094 A * | 11/1992 | Stuckart | ............... | B01D 21/283 204/157.15 |
| 5,527,460 A * | 6/1996 | Trampler | ............. | B01D 21/283 209/155 |
| 5,626,767 A * | 5/1997 | Trampler | ............. | B01D 21/283 210/748.05 |
| 5,711,888 A * | 1/1998 | Trampler | ............. | B01D 21/283 210/748.05 |
| 6,482,327 B1 * | 11/2002 | Mori | ......................... | C02F 9/00 210/695 |
| 6,749,666 B2 * | 6/2004 | Meegan, Jr. | ........... | B01D 51/08 55/318 |
| 7,223,366 B2 * | 5/2007 | Hauan | .................. | G01N 29/036 422/50 |
| 8,865,003 B2 * | 10/2014 | Yang | ..................... | B01D 21/283 210/153 |
| 9,208,270 B2 * | 12/2015 | Fontes | ................. | G06F 17/5018 |
| 10,106,770 B2 * | 10/2018 | Presz, Jr. | ................ | C12M 47/02 |
| 2004/0197227 A1 * | 10/2004 | Hauan | .................. | G01N 29/036 422/68.1 |
| 2010/0078384 A1 * | 4/2010 | Yang | ..................... | B01D 21/283 210/645 |
| 2011/0076747 A1 * | 3/2011 | Cloud | ..................... | C12M 21/02 435/257.1 |
| 2011/0258920 A1 * | 10/2011 | Licamele | ................ | A01G 33/00 47/1.4 |
| 2012/0179426 A1 * | 7/2012 | Fontes | ................. | G06F 17/5018 703/1 |
| 2012/0252105 A1 * | 10/2012 | Ahrens | ................... | C12M 21/02 435/257.3 |

(Continued)

OTHER PUBLICATIONS

Comsol, https://www.comsol.com/multiphysics/eigenfrequencyanalysis, pp. 1-28, Apr. 2018.*

*Primary Examiner* — Deborah K Ware
(74) *Attorney, Agent, or Firm* — Lewis Roca Rothgerber Christie LLP

(57) ABSTRACT

An acoustic resonator device includes a fluid chamber with a carrier surface and a reflector surface. The fluid chamber is filled with a volume of a fluid that includes a phase-separate material such as algae. The carrier surface is coupled to a transducer, which may be a lead zirconate titanate (PZT) transducer. The transducer, when supplied with electricity, emits an acoustic wave-based output of an output frequency (e.g., ultrasound). A sensor may be used to track one or more eigenfrequencies of the volume of fluid, the acoustic resonator device, or some combination thereof. A controller may receive tracking data from the sensor and control the voltage source, the transducer, or some combination thereof to ensure that the output frequency matches one of the tracked eigenfrequencies, thereby maximizing excitation of the fluid to improve efficiency of mixing, stimulation, and separation of materials from fluid (e.g., for algal biocrude production).

12 Claims, 15 Drawing Sheets

(56) References Cited

U.S. PATENT DOCUMENTS

| | | | |
|---|---|---|---|
| 2013/0116459 A1* | 5/2013 | Marrone | C11B 1/106 554/175 |
| 2016/0162617 A1* | 6/2016 | Fontes | G06F 17/5018 703/1 |
| 2016/0306908 A1* | 10/2016 | Fontes | G06F 17/5018 |
| 2019/0138675 A1* | 5/2019 | Fontes | G06F 17/5018 |

* cited by examiner

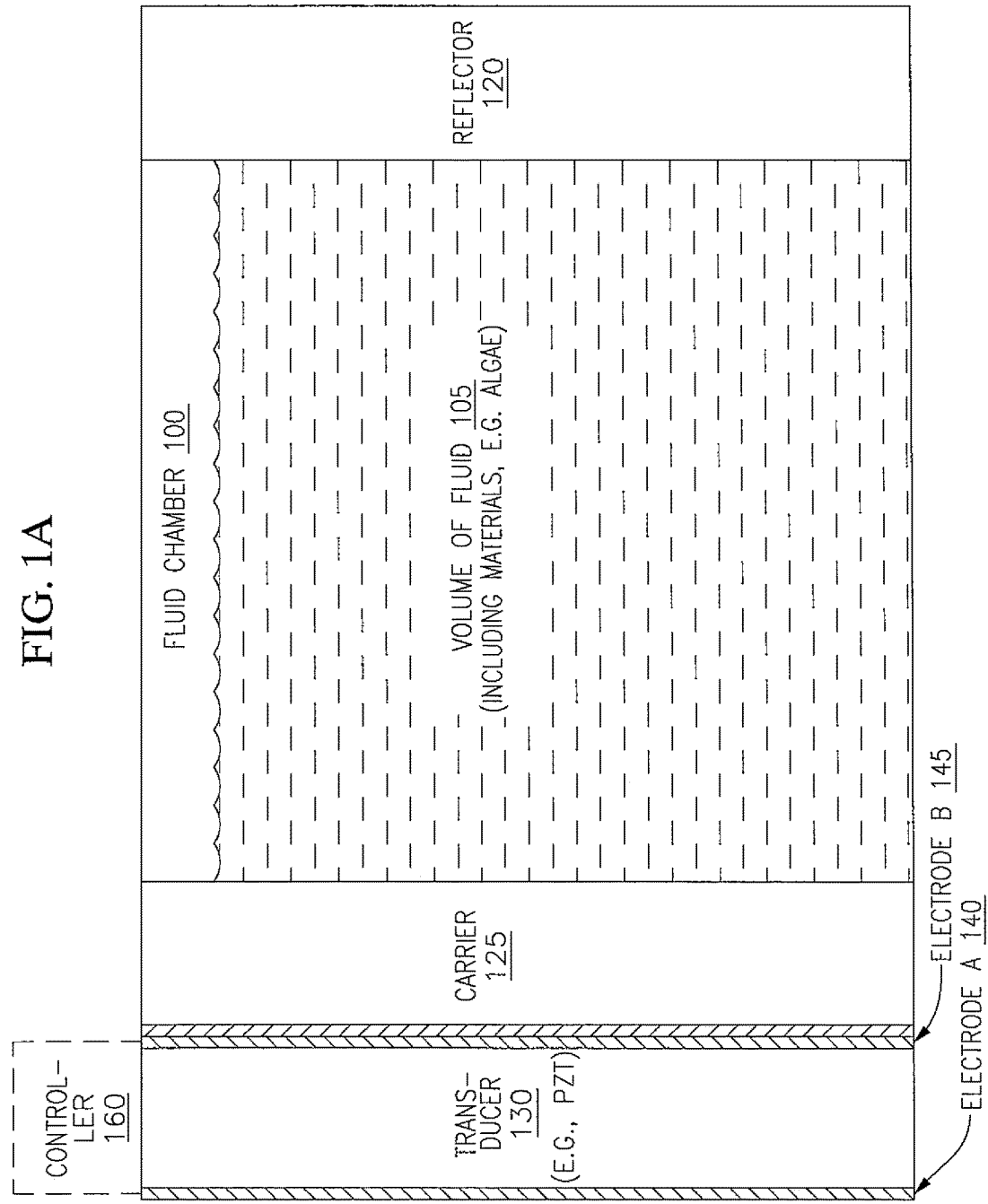

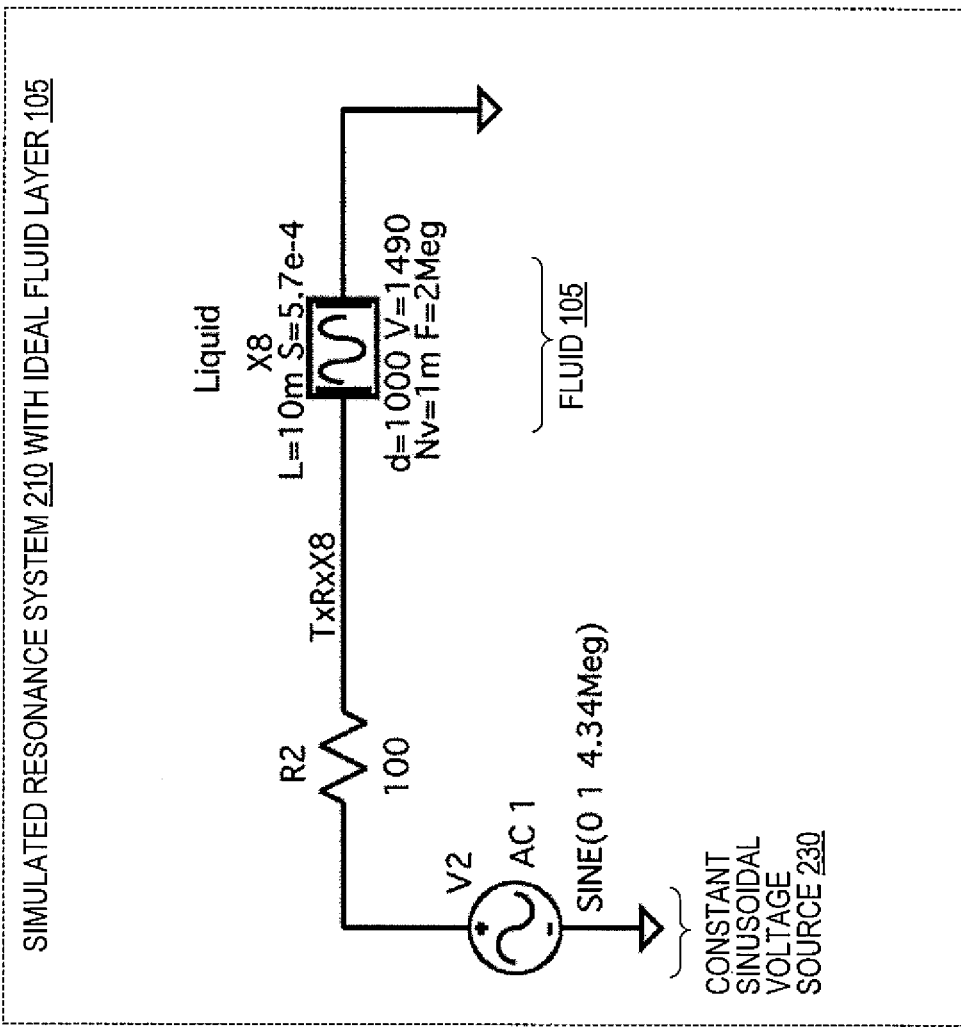

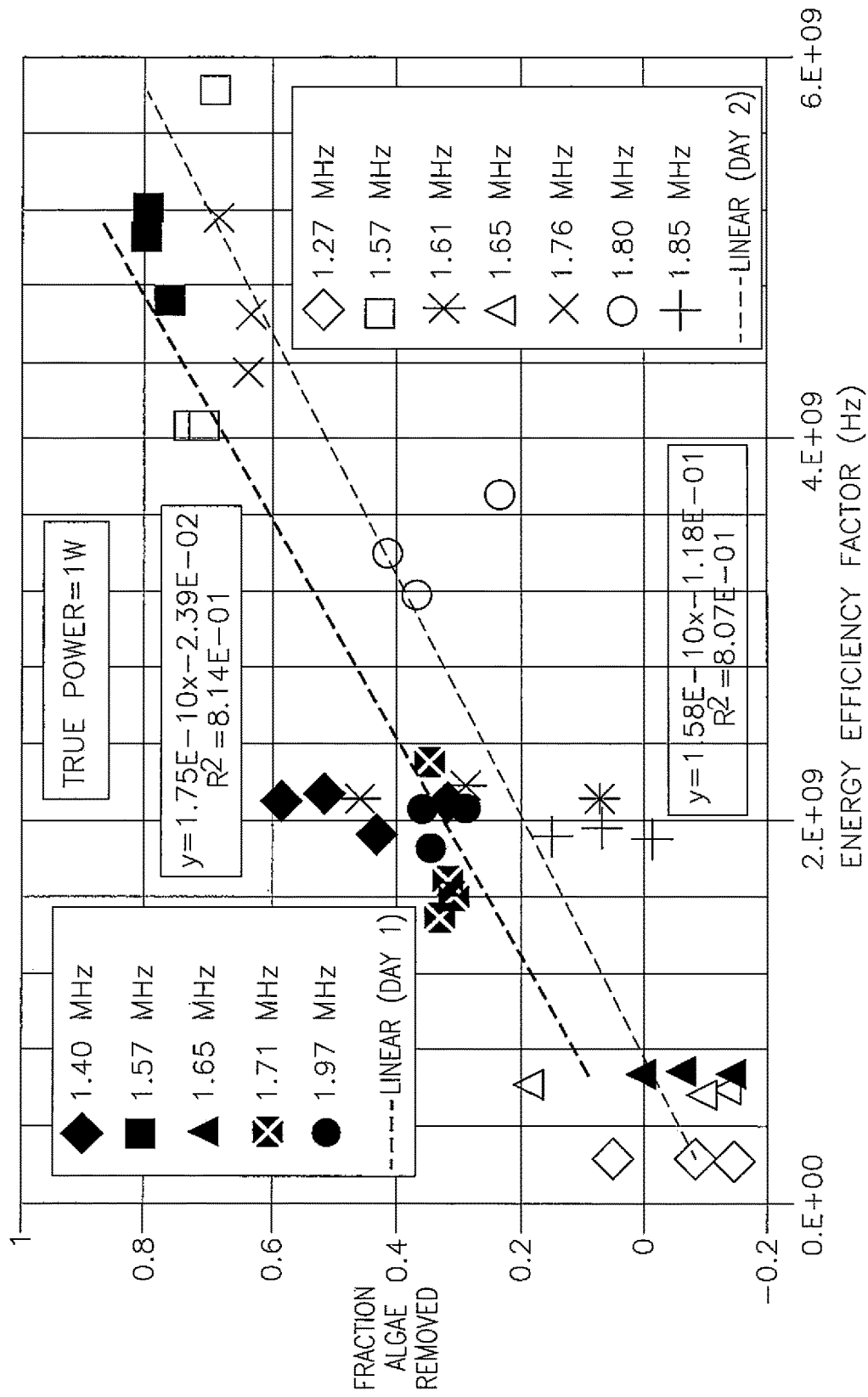

ACOUSTIC MANIPULATION OF FLUIDS BASED ON EIGENFREQUENCY

CROSS REFERENCE TO RELATED APPLICATIONS

The present application claims priority to provisional patent application Ser. No. 62/276,755, filed 8 Jan. 2016 and entitled "Acoustic Manipulation of Fluids Based on Eigenfrequency," the entirety of which is incorporated herein by reference.

STATEMENT REGARDING GOVERNMENT RIGHTS

The present invention was made with government support under Contract No. DE-AC52-06NA25396 awarded by the U.S. Department of Energy/National Nuclear Security Administration to Los Alamos National Security, LLC for the operation of Los Alamos National Laboratory. The government has certain rights in the invention.

BACKGROUND OF THE INVENTION

1. Field of the Invention

The present invention generally relates to the operation of ultrasonic devices used for mixing, stimulation, and/or separation of materials. More specifically, the present invention relates to the efficient operation of ultrasonic resonator devices for mixing, stimulating, or separating algae, algae-based byproducts and biomaterials, and other phase-separate solid, gas, and liquid materials within a continuous medium (such as a liquid or gas) based on selecting and tracking resonant frequencies in the resonator device.

2. Description of the Related Art

Alternative fuels and fuel sources are becoming more prevalent in the modern economy. For example, "biocrude" from lipid-producing microalgae has been developed as a renewable and carbon-neutral source of crude oil. Harvesting and dewatering the algae into a concentrated feedstock is a key step in the economic and energetic viability of the algal biofuel production process. However, conventional methods of concentrating microalgae from dilute algal water, such as cross-flow membrane filtration, gravity sedimentation, and centrifugation systems are generally too costly, too limited in their usefulness, and/or require more energy than is available in the microalgae being processed. These technologies often have issues requiring interruption during long-term use, such as issues with filter fouling (i.e., buildup of cells in a spin filter, limiting time of productive operation), sealability, and bacterial contamination. Often, such processes also require additional chemical additives such as flocculants and solvents in order to complete the algal biocrude harvesting and dewatering. Costs of algal biocrude production using such methods are still generally prohibitively higher than traditional crude oil production costs, yields are generally significantly lower, and efficiencies of both cost and energy usage of algal biocrude production are generally lower than traditional crude oil production methods. The United States Department of Energy's BioEnergy Technologies Office (BETO) has set targets to reduce the cost of algal biocrude by 75% by 2022. Substantial increases in efficiency and decreases in cost are required in the coming years in order to meet this goal.

Recently, methods and systems have been developed to separate or concentrate microalgae from algal water by applying an acoustic field, particularly with the use of ultrasound. Ultrasound devices benefit from having relatively simple designs and not requiring chemical additives such as flocculants and solvents in baseline processes. However, current methods and systems applying ultrasound for microalgae separation are still prohibitively inefficient both in cost and energy usage.

Therefore, there is a need for improved ultrasonic fluid manipulation devices.

SUMMARY OF THE CLAIMED INVENTION

One exemplary system for acoustic fluid manipulation includes a fluid chamber that receives a volume of a fluid, the volume of the fluid including a phase-separate material, wherein one or more eigenfrequencies characterize at least the volume of the fluid. The system also includes a carrier surface forming at least a first sidewall portion of the fluid chamber. The system also includes a reflector surface forming at least a second sidewall portion of the fluid chamber. The system also includes a transducer coupled to the carrier surface, wherein receipt of electricity at the transducer from a voltage source triggers emission of an acoustic output by the transducer, the acoustic output thereby passing through the carrier surface and the liquid chamber toward the reflector surface, the acoustic output characterized by an output frequency that is based on the one or more eigenfrequencies, the transmission of the acoustic wave thereby exciting at least the volume of fluid.

Additional features and advantages of the inspection system of the preferred embodiment are described in detail below with reference to the following drawings.

BRIEF DESCRIPTION OF THE FIGURES

FIG. 1A illustrates an exemplary acoustic resonator device with a transducer.

FIG. 2C is an electronic circuit diagram simulating a resonance system in which a waveform is ideally transferred into a volume of fluid without interference or use of any other components.

FIG. 8D is a graph charting a fraction of algae removed from the algal water when subjected to an acoustic standing wave when the example device is operated at a predetermined frequency, power output, and fixed time.

DETAILED DESCRIPTION OF THE EXAMPLE EMBODIMENTS

Figure 1B:
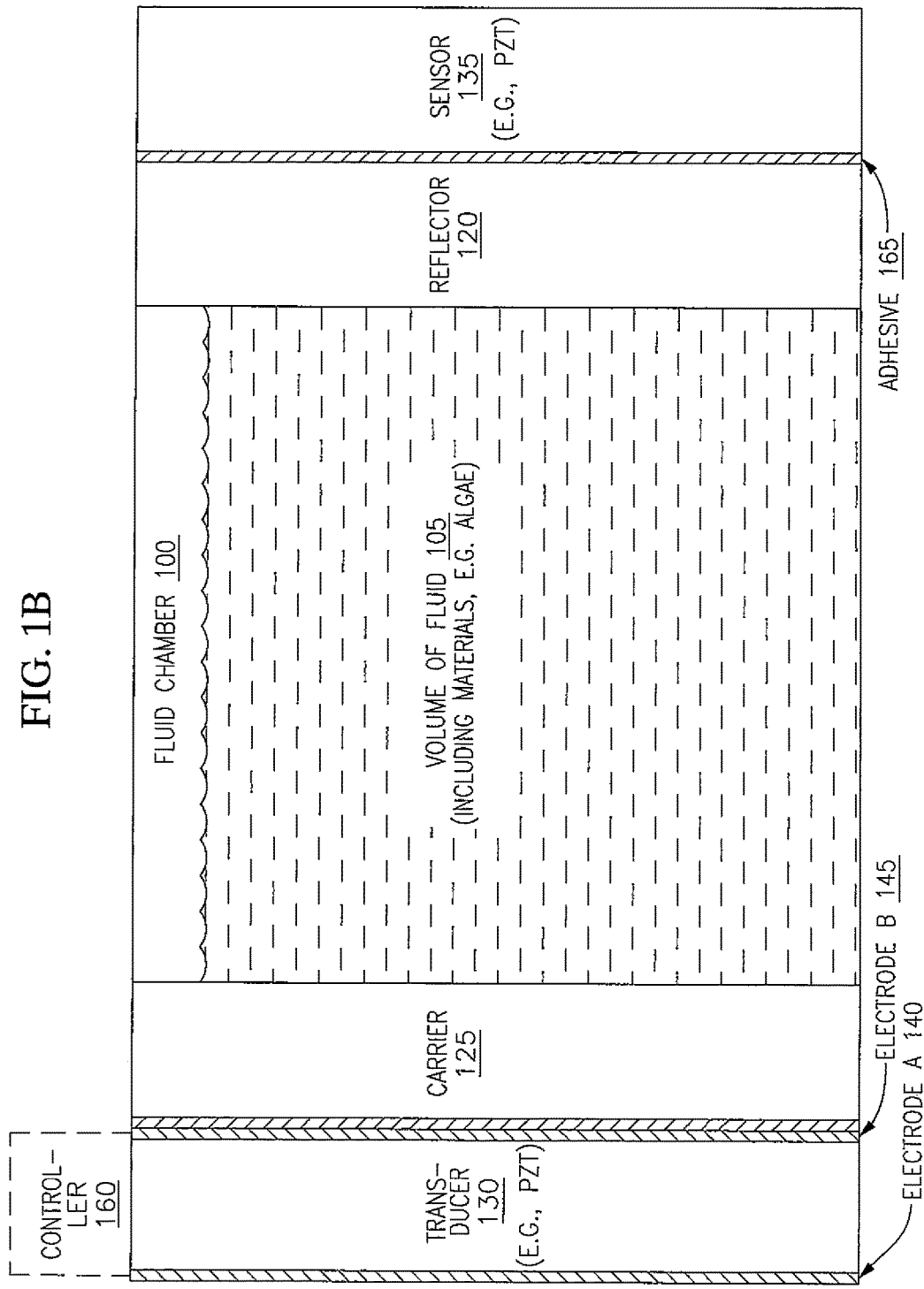
FIG. 1B illustrates an exemplary acoustic resonator device with a transducer and a sensor.

In accordance with the description of the following example and preferred embodiments, an acoustic resonator device includes a fluid chamber with a carrier surface and a reflector surface. The fluid chamber is filled with a volume of a fluid that includes a phase-separate material such as algae in a water-based medium. The carrier surface is coupled to a transducer, which may be a lead zirconate titanate (PZT) transducer. The transducer, when supplied with electricity, emits an acoustic wave-based output of an output frequency (e.g., ultrasound).

A sensor may be used to track one or more eigenfrequencies of the volume of fluid, the acoustic resonator device, or some combination thereof. In some embodiments, the transducer can also function as a sensor or as one of multiple sensors. A controller may receive tracking data from the sensor and control the voltage source, the transducer, or some combination thereof to ensure that the output frequency matches one of the tracked eigenfrequencies, thereby maximizing excitation of the fluid to improve efficiency of mixing, stimulation, and separation of materials from fluid (e.g., for algal biocrude production). The fluid may include a liquid, a gas, or some combination thereof.

The output frequency may be controlled to maximize excitation of at least part of the acoustic resonator including the volume of fluid in its entirety, of a particular region of the volume of fluid, of phase-separate materials (themselves including one or more solids, liquids, gases, or some combination thereof) within the fluid, This may be used, among other purposes, to enhance the efficiency of harvesting microalgae from algal fluids for algal biocrude production. These and many other uses and benefits of the claimed invention are described below in detail with reference to the appended Figures.

FIG. 1A illustrates an exemplary acoustic resonator device with a transducer. In particular, the acoustic resonator device of FIG. 1A includes a fluid chamber 100, inside which may be stored a volume of a fluid 105. The fluid 105 may include one or more liquids (e.g., water, oil), one or more gases (e.g., air, carbon dioxide, oxygen, nitrogen, hydrogen, helium, noble gases), or some combination thereof. The fluid 105 includes an amount of a material mixed in, which may be phase-separate from the volume of fluid. The material may include one or more solids, one or more liquids, one or more gases, or some combination thereof. For example, the material may include a number of lipid-producing microalgae. The material may include solid particles (e.g. powders, granules), or may include liquids (e.g., water-based, lipid-based, alcohol-based), or may include gases (e.g., gas bubbles), or may include some combination thereof (e.g., inorganic multimaterial structures, living/dead cells, microalgae, bacteria, viruses). The material (e.g., the microalgae) may be distributed relatively uniformly throughout the volume of fluid 105. Alternately, the volume of fluid 105 may include one or more areas of relatively higher-than-average concentrations of the material (e.g., the microalgae) and/or one or more areas of lower-than-average concentrations of the material (e.g., the microalgae).

In various example configurations, the fluid chamber 100 may take one of many forms, such as a cube, a rectangular prism, a cylinder, a sphere, a polygonal prism (based on a polygon with any number of sides), a polyhedron with any number of sides, or some combination thereof (e.g., the shape of the fluid chamber 100 may be created by coupling or overlapping two or more of the previously-recited exemplary shapes).

The example acoustic resonator device shown in FIG. 1A can include a carrier 125, which may be a planar or curved plate or layer of material, such as glass or plastic, that forms at least one side of the fluid chamber 100. The example acoustic resonator device shown in FIG. 1 can also include a reflector 120, which likewise may be a planar or curved plate or layer of material, such as glass or plastic, that forms a second side of the fluid chamber 100. In some cases, the carrier 125 and reflector 120 may be separate components (e.g., separate pieces of glass or plastic), while in other cases, the carrier 125 and reflector 120 may simply be terms describing different sections of the same component (e.g., the same piece of glass or plastic), such as when the carrier 125 and reflector 120 are part of a unibody exterior to the fluid chamber 100 (e.g., such as when the fluid chamber 100 is cylindrical).

In one example configuration, a transducer 130 is secured to the carrier 125. A layer of adhesive 165 is used for this purpose in FIG. 1A, but in other cases, transducer 130 may be secured to the carried 125 in some other way not requiring the layer of adhesive 165. The transducer 130 may, for example, include a piezoelectric ceramic substance such as lead zirconate titanate ("PZT") (Pb[$Zr_x Ti_{1-x}$]$O_3$ $0 \le x \le 1$) or a substance with similar properties. The transducer 130 may include or function alongside two electrodes, labeled electrode A 140 and electrode B 145 in FIG. 1A. The two electrodes may be used to trigger movement of the transducer 130 to generate acoustic waves of a predetermined wavelength and frequency at a predetermined power output, which then travel through the carrier 125, through the volume of fluid 105, and reflect from the reflector 120 to produce a standing wave. In some cases, one electrode (e.g., electrode A 140 or electrode B 145) may be enough, or in other cases, more than one or more than two electrodes may be used. In some embodiments, the transducer 130 can function both as a generator of ultrasonic waves as well as a sensor of one or more eigenfrequencies of the volume of fluid 105 and/or acoustic resonator.

While the carrier 125 (e.g., with its coupled transducer 130) and reflector 120 are illustrated in FIG. 1A and FIG. 1B as horizontal sidewalls of the fluid chamber 100, it should be understood that this is exemplary rather than required. In another embodiment, the carrier 125 (e.g., with its coupled transducer 130) may be a bottom wall (a "floor") of the fluid chamber 100 while the reflector 120 is a top wall (a "ceiling") of the fluid chamber 100, or vice versa, thereby orienting the output sound wave vertically relative to the orientation of the fluid chamber 100 as drawn in FIG. 1A and FIG. 1B. In an embodiment where the fluid chamber 100 is a more complex polyhedron (e.g., an icosahedron or octahedron), the carrier 125 (e.g., with its coupled transducer 130) and reflector 120 may represent opposing diagonally-oriented sidewalls, thereby orienting the output sound wave diagonally relative to the orientation of the fluid chamber 100 as drawn in FIG. 1A and FIG. 1B.

The sound waves (e.g., ultrasonic waves) generated by the transducer 130 may propagate through the carrier 125, through the volume of fluid 105 (which may include algae) within its fluid container 100, and toward the reflector 120. The sound waves propagate towards the reflector 120 and then in the reverse direction towards the carrier 125 to produce a standing wave, which creates forces that effectively excite at least a subset of the volume fluid 105 and its included materials (e.g., which may include algae as previously discussed), which allows for operations such as mixing the materials in the volume of fluid 105, stimulation of the materials and/or the volume of fluid 105, separation of the materials from the volume of fluid 105, or some combination thereof.

As shown in FIGS. 1A and 1B, a controller 160 may select and control the frequencies/wavelengths and amplitudes of the sound waves output by the transducer 130 by tracking eigenfrequencies corresponding to at least the volume of fluid 105 and by selecting the frequencies of the output sound waves based on the tracked eigenfrequencies. The tracked eigenfrequencies may characterize the volume of fluid 105 within its boundary conditions; namely, the tracked eigenfrequencies may characterize the volume of fluid 105 in addition to at least a subset of the acoustic resonator system (e.g., the eigenfrequencies may characterize the volume of fluid 105 as well as the carrier 125 and/or the reflector 120 and/or the adhesive 165 and/or the transducer 130 and/or the sensor 135 and/or the electrode A 140 and/or the electrode B 145 and/or the controller 160). Secondary eigenfrequencies corresponding to at least a subset of the acoustic resonator system without the volume of fluid 105 (i.e., the acoustic resonator system with an empty fluid chamber containing only air 100) may also be factored into selection and control of the frequencies/wavelengths of the sound wave output by the transducer 130 to increase electrical efficiency, to decrease energy loss from heat, and to increase efficiency of the mixing, stimulation, and separation operations as described below.

As shown in FIGS. 1A and 1B, the controller 160 may be communicatively coupled to the transducer 130 and/or to the two electrodes (i.e., electrode A 140 and electrode B 145) and may, for example, be used to control the movement of the transducer 130 in a manner that controls the wavelength and frequency of the acoustic waves (e.g., standing wave) generated by the movement of the transducer 130. While the controller 160 is illustrated in FIG. 1A as being located directly above the transducer 130, the controller 160 may in other cases be coupled to another portion of the acoustic resonator device or may be external to the acoustic resonator device and control the transducer 130 via a wired connection or via a wireless connection (e.g., Bluetooth, Wi-Fi, radio-frequency communications, or near-field-communications).

Figure 7:
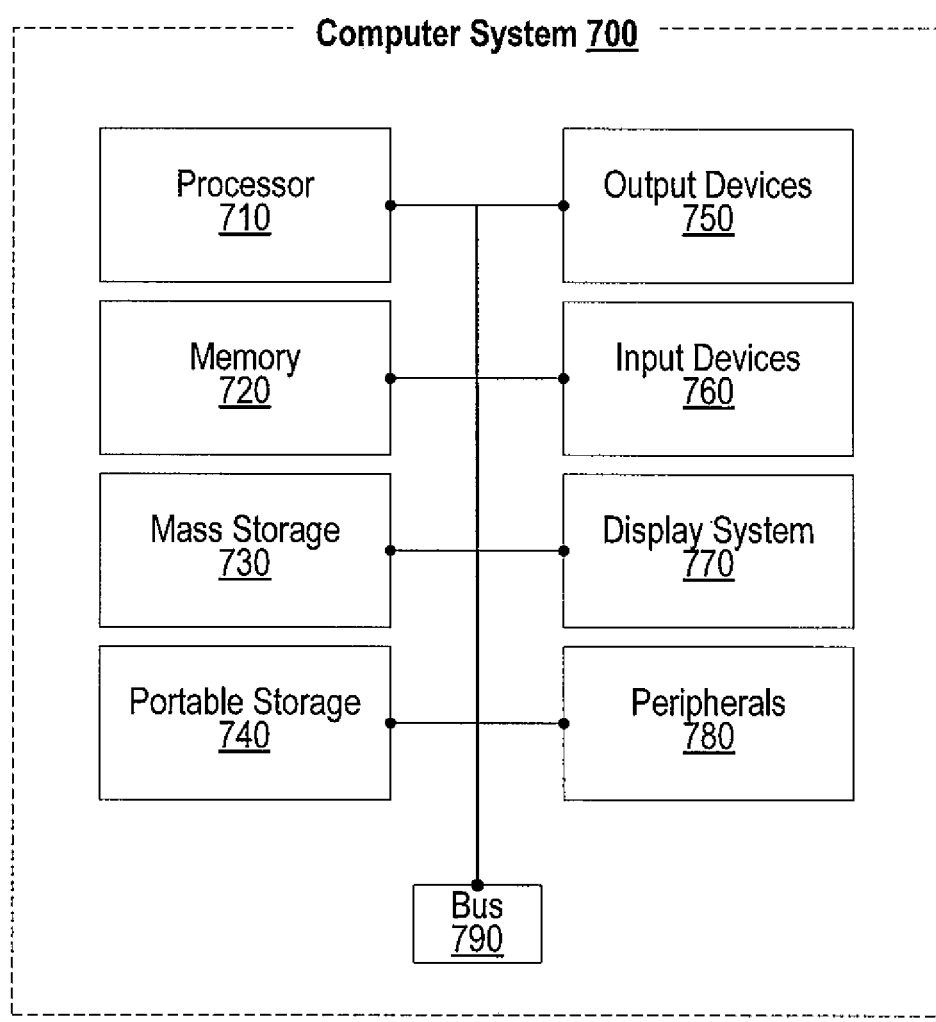
FIG. 7 is a block diagram of an exemplary computing device that may be used to implement a controller in accordance with one or more example embodiments of the present invention.

The controller 160 may be a variant of computer system 700 identified in FIG. 7 or its description, or may include at least a subset of the hardware components and software elements identified in FIG. 7 or its description. The user device 500 may include one or more memory and/or data storage module(s) 510 (e.g., which may include any kind of memory 720, mass storage 730, portable storage 740, or some combination thereof), one or more processor(s) 505 (e.g., processor 710), one or more input mechanism(s) (e.g., one or more input devices 760), one or more display screen(s) (e.g., such as display system 770), or some combination thereof. The controller 160 may include one or more communication element(s) 515 which may include a communication receiver, a communication transmitter, a communication transceiver, or some combination thereof, and which may send and/or receive data using wired data transfer methods (e.g., Ethernet, "USB" Universal Serial Bus cable, "HDMI" High-Definition Multimedia Interface cable, Apple lightning cable), wireless data transfer methods (e.g., Bluetooth, 802.11 Wi-Fi, 3G/4G/5G/LTE cellular networks), or some combination thereof. The controller 160 may be a physical system or a virtual system. In some variations of the example embodiment, the controller 160 may include an amplifier designed to boost the voltage provided to the transducer 130.

FIG. 1B illustrates an exemplary acoustic resonator device with a transducer and a sensor. The acoustic resonator device of FIG. 1B is similar to the acoustic resonator device of FIG. 1A with the addition of a sensor 135. The sensor 135 may be coupled to the reflector 120 as pictured in FIG. 1B, or may alternately be coupled to the carrier 125 (not pictured). The sensor 135 may also include a piezoelectric ceramic substance such as lead zirconate titanate ("PZT") ($Pb[Zr_xTi_{1-x}]O_3$ $0 \le x \le 1$) or a substance with similar properties. Alternative sensors 135 can include for example an optical displacement sensor, including for example any suitable sensor or combination or sensors such as light transmission or light scattering sensors that are sensitive to the concentration of algae or other particles in the fluid. Other suitable sensors 135 can include a microphone, a speaker, an accelerometer (PZT, PVDF, or quartz crystal), a laser vibrometer, or any suitable combination thereof. In one example configuration, the sensor 135 may be communicatively coupled to the controller 160 and/or to the transducer 130. A layer of adhesive 165 is used for the purpose of securing the sensor 135 to the reflector 120 in FIG. 1B, but in other cases, the sensor 135 may be secured to the carried 125 in some other way not requiring the layer of adhesive 165.

The sensor 135 may produce an output (e.g., in the form of an electrical signal) that may be transmitted to the controller 160 and/or to the transducer 130. The sensor 135 may be used to track the resonance of the volume of fluid 105 and/or the boundary conditions of the volume of fluid 105 (e.g., including the reflector 120, the carrier 125, the adhesive 165, the transducer 130, the sensor 135, the electrode A 140, the electrode B 145, the controller 160, or some combination thereof) via vibrations detected by the sensor 135 (e.g., exactly what portion of the acoustic resonance device and its volume of fluid 105 the tracked eigenfrequencies characterize may be based on where the sensor 135 is located). The sensor 135 may work by converting pressure produced by the acoustic waves generated by the transducer 130, and any resulting resonance, into an electrical current for which properties (e.g., voltage) may vary based on the properties (e.g., wavelength, frequency, amplitude, phase) of the detected acoustic waves. Alternative sensors 135, such as optical scattering and/or optical transmission sensors, can function by generating an electrical signal in response to a received optical signal indicative of the concentration or presence of algae or other particles in the fluid.

As noted above, the separate sensor 135 illustrated in FIG. 1B is optional even when a sensor 135 is desired, because in some cases, a PZT element (that is acting as the transducer 130) may also act as the sensor 135, either simultaneously or at alternating times or some combination thereof. In such a case, the acoustic resonator device may look more like the one illustrated in FIG. 1A, but with the PZT labeled transducer 130 performing both functions as both the transducer 130 and the sensor 135. The acoustic resonator device may also have multiple sensors 135—for example, it may have a separate sensor 135 as illustrated in FIG. 1B as well as a transducer 130 that doubles as a sensor 135 (e.g., in the interests of increasing accuracy and/or precision and/or detection frequency).

The frequencies of sound emitted by the transducer 130 should match or come close to (e.g., within a predetermined number of hertz or megahertz) the eigenfrequencies of system elements (e.g., eigenfrequencies of the acoustic resonator device as a whole, eigenfrequencies of the transducer 130 in situ, eigenfrequencies of a PZT component of the transducer 130 in particular, eigenfrequencies of at least some of the volume of fluid 105, eigenfrequencies of material such as algae within the volume of fluid 105) as measured and tracked by the sensor 135 (and/or with additional sensors that are not shown in FIG. 1B). In most cases, data (e.g., measured eigenfrequencies) from the sensor 135 should be substantially the same (or at least similar) whether the sensor 135 is in the form of a second PZT coupled to the reflector 120 as illustrated in FIG. 1B or whether the sensor 135 is a secondary function of the PZT used in the transducer 130 as in FIG. 1A.

While the fluid chamber 100 of the acoustic resonator devices of FIG. 1A and FIG. 1B are illustrated as only partially filled with a liquid, marked as the fluid 105, this illustration should be construed as exemplary rather than limiting. Ordinary usage of the acoustic resonator device may in some cases be improved by having the fluid chamber 100 be entirely or almost entirely full of the fluid 105 so as to minimize possible interference of other substances such as air 230, particularly when the sensor 135 is used to track resonance and eigenfrequencies related to the fluid 105 in the fluid chamber 100. On the other hand, the fluid 105 may include both liquids and gases (e.g., as may occur if the volume of fluid 105 includes a liquid at or near its boiling point), in which case the fluid chamber 100 as illustrated in FIG. 1A and FIG. 1B may indeed be full of fluid. In some cases the volume of fluid 105 may include some solids as well (e.g., as may occur if the volume of fluid 105 includes a liquid near a freezing point or a solid near a sublimation point).

Figure 2A:
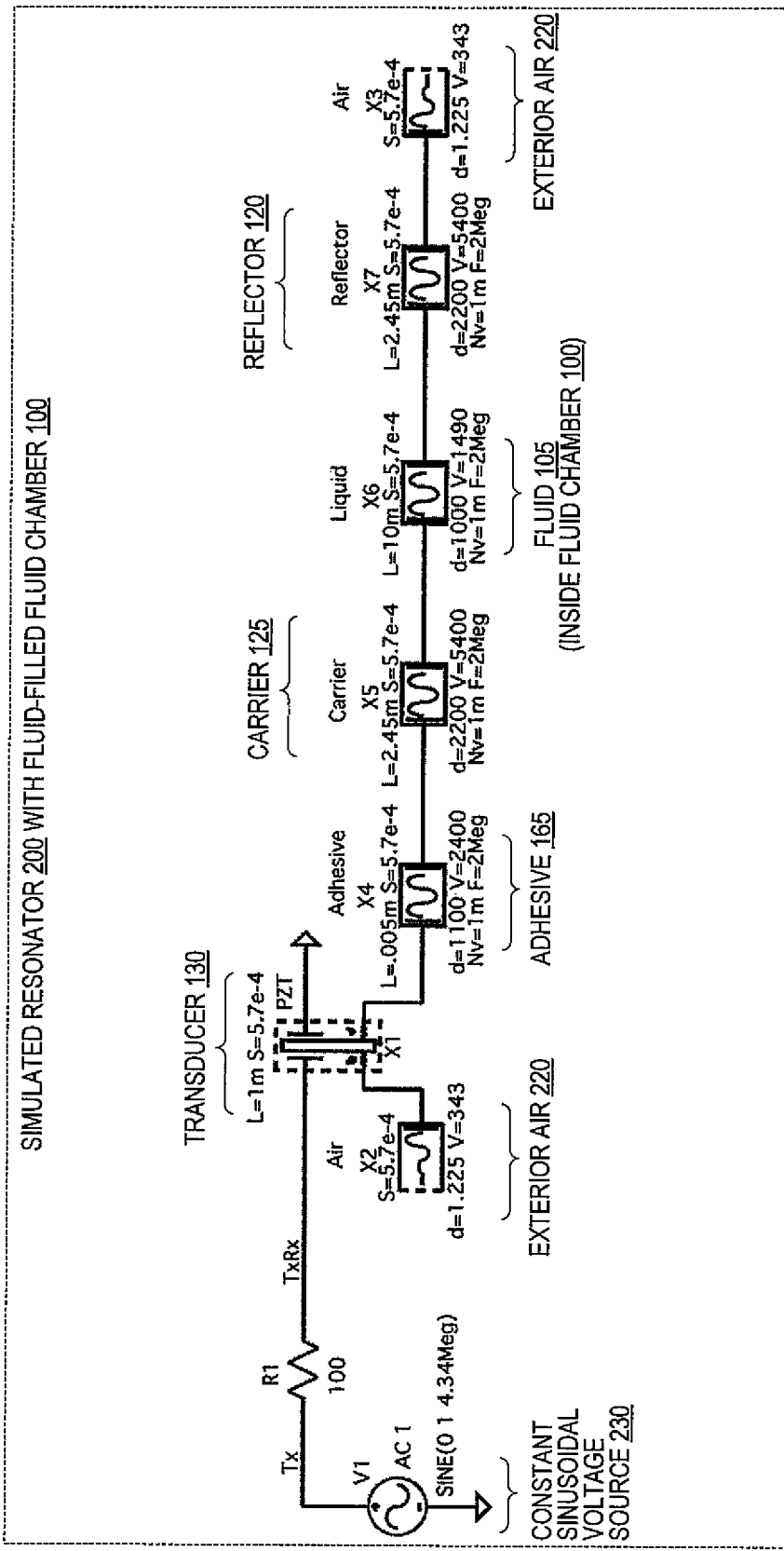
FIG. 2A is an electronic circuit simulating an exemplary acoustic resonator device with a fluid-filled fluid chamber.

FIG. 2A is an electronic circuit simulating an exemplary acoustic resonator device with a transducer and with volume of fluid in the fluid chamber. The electronic circuit simulation of FIG. 2A represents an electronic circuit simulation of the acoustic resonator device illustrated in FIG. 1A, with the fluid chamber 100 filled entirely (or almost entirely) with volume of fluid 105.

The electronic circuit simulation of the acoustic resonator device 200 of FIG. 2A is a design produced in SPICE (Simulation Program with Integrated Circuit Emphasis). The simulated acoustic resonator device 200 of FIG. 2A includes elements simulating the volume of fluid 105 (e.g., illustrated with identified properties similar to liquid water), the carrier 125 (e.g., illustrated with identified properties similar to glass), the reflector 120 (e.g., also given properties similar to glass), the transducer 130 (e.g., illustrated with identified properties similar to PZT), an adhesive 165 affixing the transducer 130 to the carrier 125, a constant sinusoidal voltage source 230 supplying power to the transducer 130, and even factors in exterior air 220 outside of the simulated acoustic resonator device 200. A resonance result produced by the simulated acoustic resonator device 200 of FIG. 2A is charted in the graph of FIG. 5 as the light grey line 510.

Figure 2B:
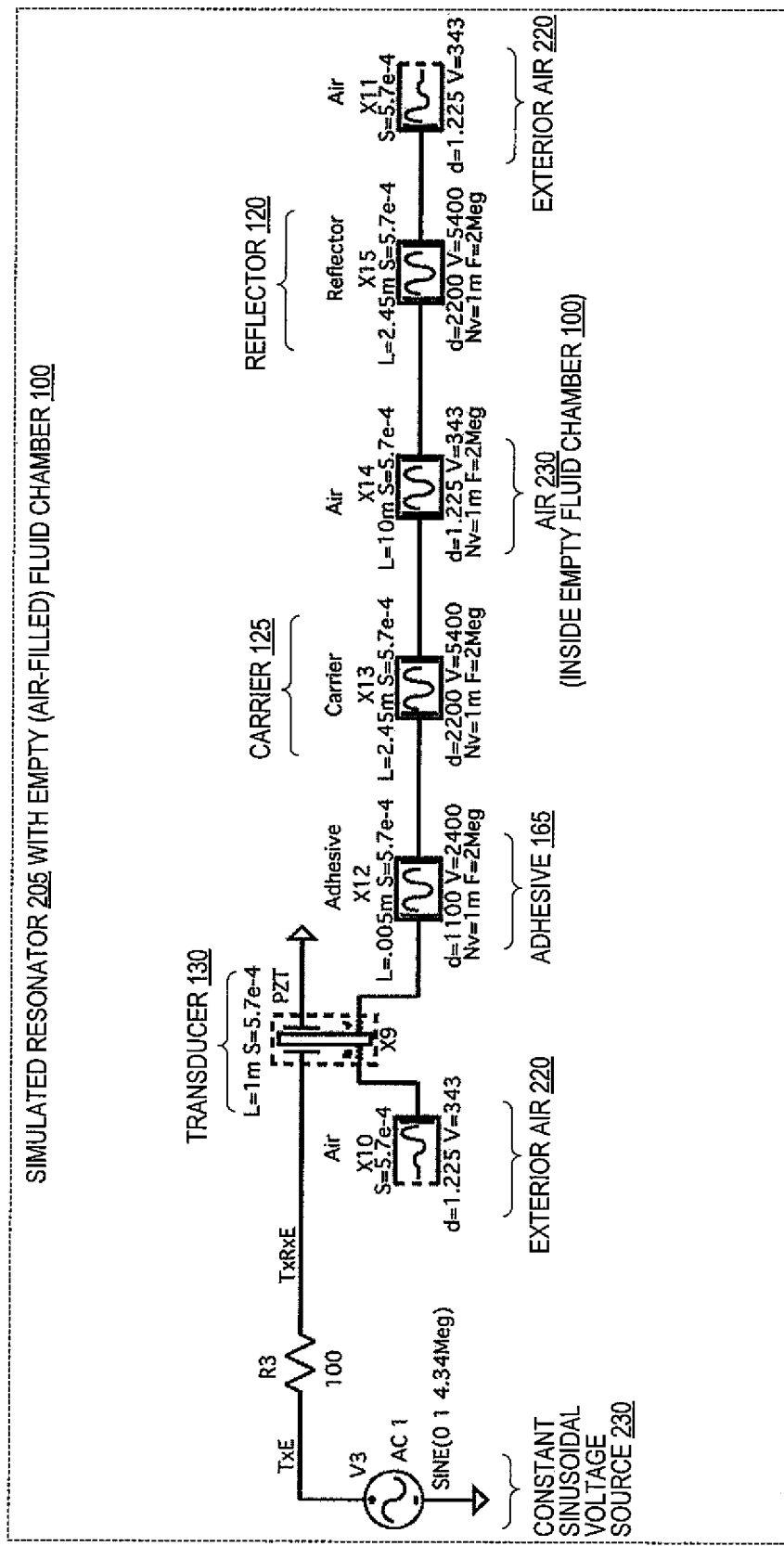
FIG. 2B is an electronic circuit simulating an exemplary acoustic resonator device with an empty (air-filled) fluid chamber.

FIG. 2B is an electronic circuit diagram simulating an exemplary acoustic resonator device with a transducer and with air in the fluid chamber. The simulated acoustic resonator device 205 illustrated in FIG. 2B is similar to the simulated acoustic resonator device 200 illustrated in FIG. 2A but instead illustrates air 230 in place of the volume of fluid 105, indicating that that fluid chamber 100 is empty in the simulated acoustic resonator device 205 of FIG. 2B. A resonance result produced by the simulated acoustic resonator device 205 of FIG. 2B is charted in the graph of FIG. 5 as the medium grey line 520.

FIG. 2C is an electronic circuit diagram simulating a resonance system in which a waveform is ideally transferred into a volume of fluid without interference or use of any other components. The simulated resonance system 210 of FIG. 2C simply transfers the waveform from the constant sinusoidal voltage source 230 directly into the volume of fluid 105. A resonance result produced by the simulated acoustic resonance system 210 of FIG. 2C is charted in the graph of FIG. 5 as the black line 530.

Figure 3A:
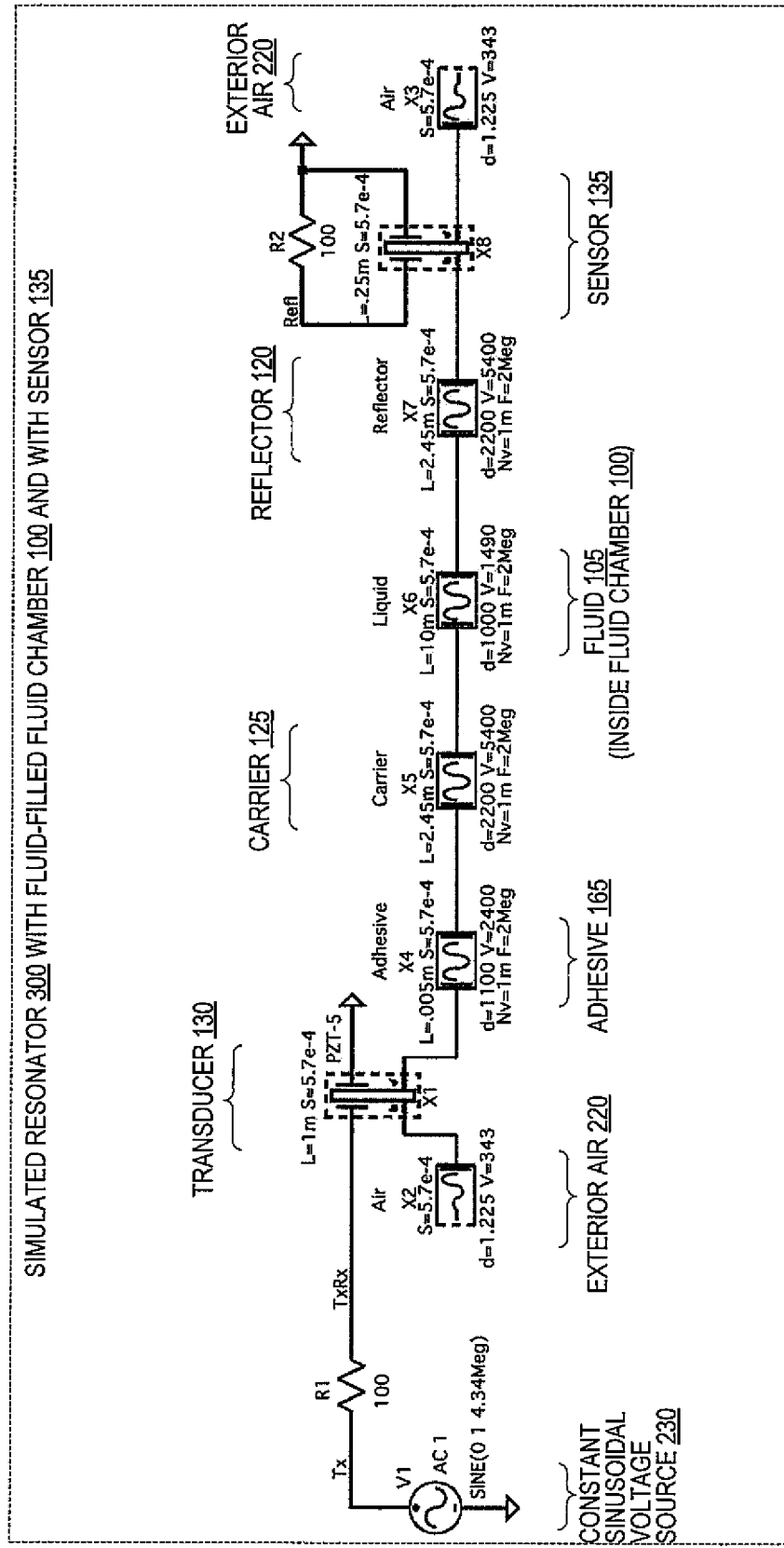
FIG. 3A is an electronic circuit simulating an exemplary acoustic resonator device with a transducer and a sensor and with a volume of fluid in the fluid chamber.

FIG. 3A is an electronic circuit simulating an exemplary acoustic resonator device with a transducer and a sensor and with a volume of fluid in the fluid chamber. The simulated acoustic resonator device 300 illustrated in FIG. 3A is similar to the simulated acoustic resonator device 200 illustrated in FIG. 2A but instead illustrates the addition of a sensor 135 mounted on the reflector 120 illustrated in FIG. 1B. A resonance result produced by the simulated acoustic resonator device 300 of FIG. 3A is charted in the graph of FIG. 6 as the light grey line 610. A sensor voltage output of the sensor 135 of the simulated acoustic resonator device 300 of FIG. 3A is charted in the graph of FIG. 6 as the black line 630.

Figure 3B:
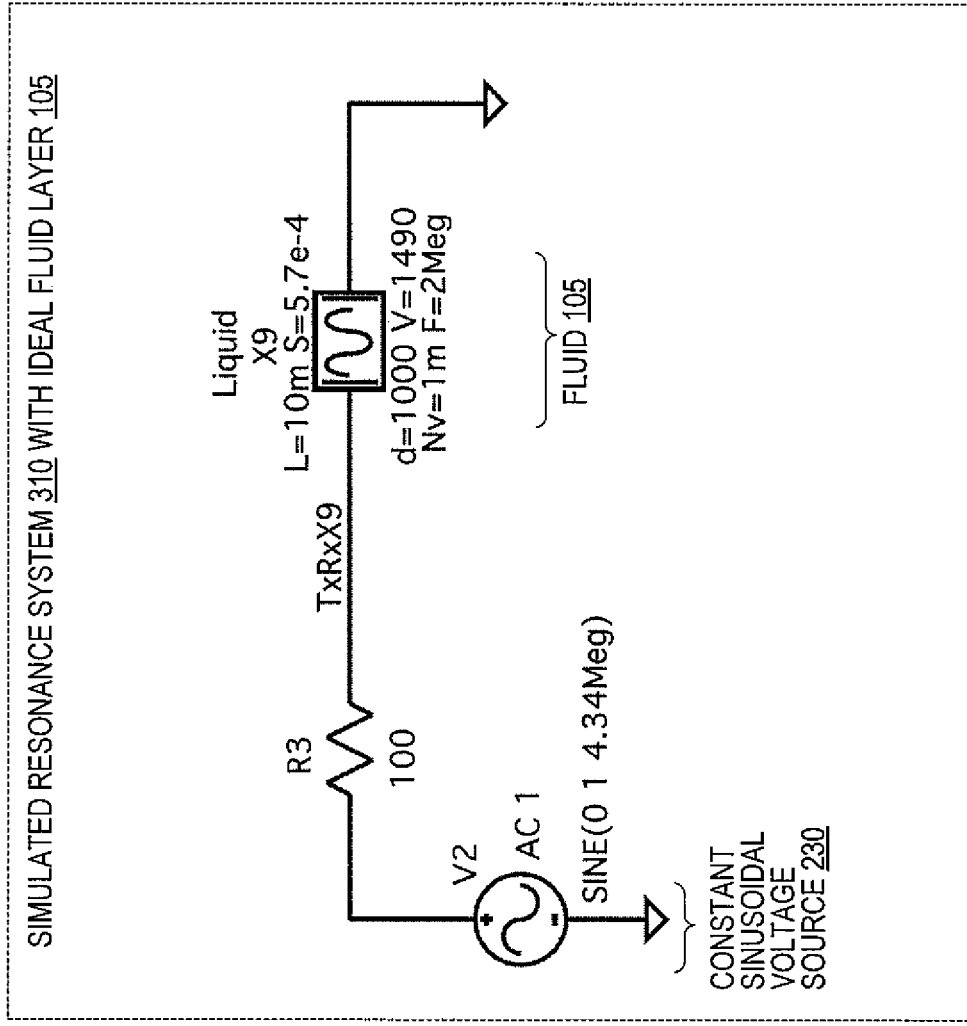
FIG. 3B is an electronic circuit diagram simulating a resonance system in which a waveform is ideally transferred into a volume of fluid without interference or use of any other components.

FIG. 3B is an electronic circuit diagram simulating a resonance system in which a waveform is ideally transferred into a volume of fluid without interference or use of any other components similarly to the electronic circuit diagram of FIG. 2C. The simulated resonance system 310 of FIG. 3B simply transfers the waveform from the constant sinusoidal voltage source 230 directly into the volume of fluid 105. A resonance result produced by the simulated acoustic resonance system 310 of FIG. 3B is charted in the graph of FIG. 6 as the medium grey line 620.

Figure 4:
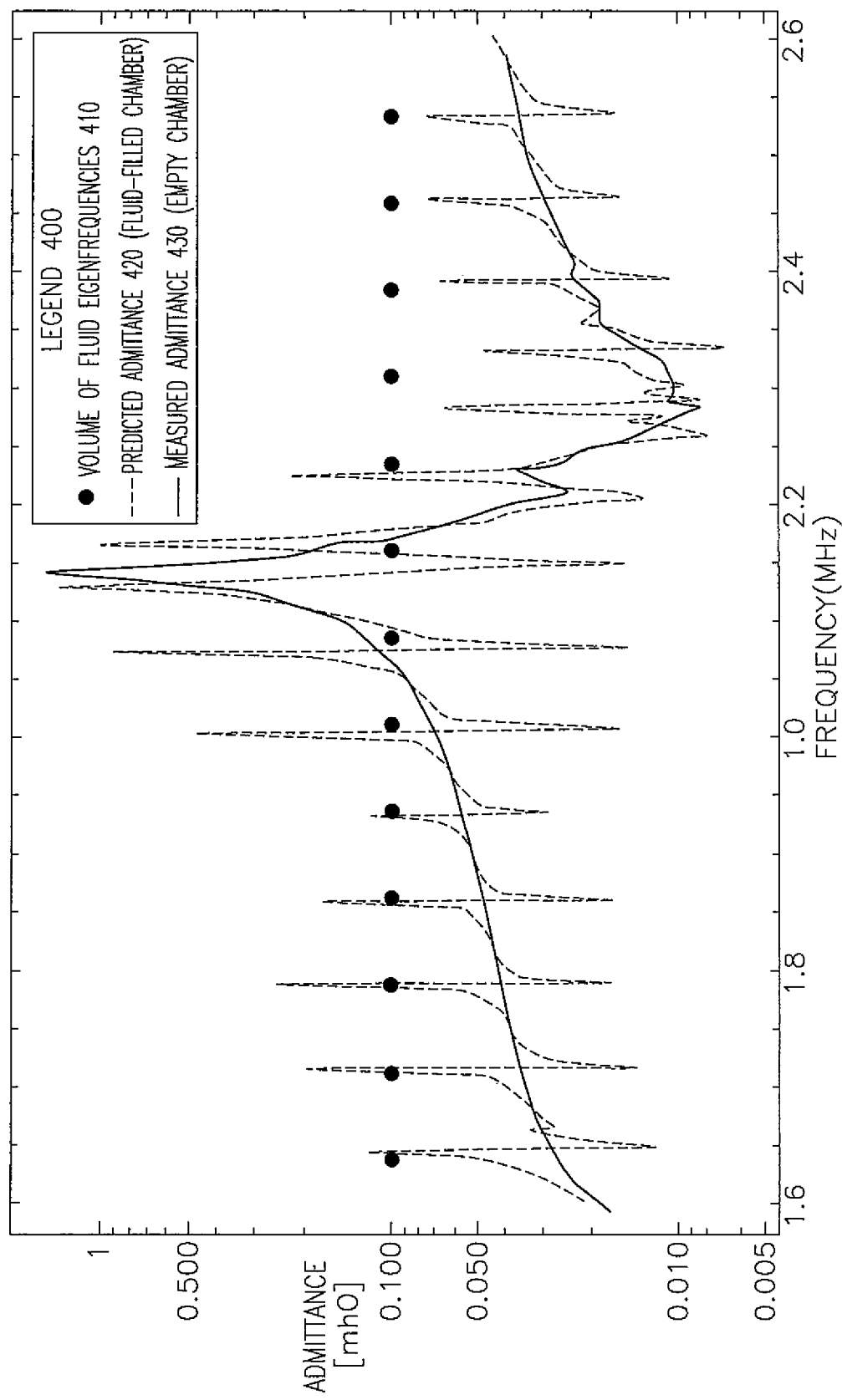
FIG. 4 is a graph charting admittance values (measured in siemens) against frequencies (measured in megahertz) and also identifies fluid eigenfrequencies.

FIG. 4 is a graph charting admittance values (measured in siemens) against frequencies (measured in megahertz) and also identifies fluid eigenfrequencies. The transducer 130 of the acoustic resonator system emits a particular frequency of sound wave(s), which may be primarily ultrasound sound wave(s). In some cases, they may include sound wave(s) in the human-audible sound range or infrasound sound wave(s) in addition to and/or in place of ultrasonic sound wave(s).

The controller 160 may be used to control what frequency or frequencies of sound wave(s) are emitted by the transducer 130, and in some cases may also control the amplitude of the sound wave(s) emitted by the transducer 130. Selecting different frequencies can produce different results in the operation of the acoustic resonator.

The solid line 430 of FIG. 4, as indicated in the legend 400, charts a measured admittance of an exemplary acoustic resonator device with a fluid chamber 100 that is empty (e.g., not full of fluid 105) and filled with air 230 (e.g.

similarly to the simulated acoustic resonator 205 of FIG. 2B). The eigenfrequency peak apparent in the solid line 430 is thus a combined eigenfrequency of the transducer 130 (including the PZT), the carrier 125, the reflector 120, the adhesive 165, and the two electrodes (electrode A 140 and electrode B 145).

The acoustic resonator device, when the fluid chamber 100 is empty, according to the solid line 430, has a resonant frequency less than three megahertz (MHz). As shown in the solid line 430 of FIG. 4, the admittance of the acoustic resonator device (solid line 430) spikes around this resonant frequency. In effect, the transducer 130 becomes easier and more electrically efficient to excite when a sound wave frequency is chosen that matches a resonant frequency (an eigenfrequency) of the PZT (and/or the remainder of the acoustic resonator including the glass/plastic of the carrier 125 and reflector 120).

In some embodiments therefore, the controller 160 functions to select a sound wave frequency near a resonant frequency of the transducer 130 (or the acoustic resonator device generally, or the PZT of the transducer 130 specifically) in order to increase electrical efficiency of the acoustic resonator device.

Because impedance goes down with a frequency near an eigenfrequency of the transducer 130 (or the acoustic resonator device generally, or the PZT of the transducer 130 specifically), however, and assuming a constant voltage source (such as the constant sinusoidal voltage source 230), a dramatic increase in current can result, which in some cases ultimately produces wasted energy in the form of heat. Therefore, in alternative embodiments, the controller 160 functions to select a sound wave frequency away from a resonant frequency of the transducer 130 (or the acoustic resonator device generally, or the PZT of the transducer 130 specifically) in order to reduce heat-based energy waste.

Tracking an eigenfrequency of the volume of fluid 105 (with or without its boundary conditions) that is away from an eigenfrequency of the empty acoustic resonator has the added benefit of bringing the eigenfrequency of the fluid-filled acoustic resonator close to the eigenfrequency of the volume of fluid 105 itself. This is visible in FIG. 5 and FIG. 6. Because the sensor 135 and/or transducer 130 tracks the eigenfrequency of the fluid-filled acoustic resonator rather than the eigenfrequency of the volume of fluid 105 itself (e.g., see black line 630 tracking light grey line 610 in FIG. 6), keeping away from the eigenfrequency of the empty acoustic resonator essentially means that the sensor 135 and/or transducer 130 can be used to track the eigenfrequency closer to that of the volume of fluid 105 itself, allowing the controller 160 to keep the transducer 130 emitting sound waves at a frequency that is optimal for harvesting materials (e.g. algae) in the volume of fluid 105 (or for mixing the materials in the volume of fluid 105 or stimulating the volume of fluid 105 and/or its materials).

The circles 410 of FIG. 4 identify eigenfrequencies of the volume of fluid 105 (calculated from first principles using the wave propagation velocity, length of fluid layer 105, and the wavelength in ½ wavelength increments), the volume of fluid 105 including materials (e.g., microalgae harvested for generation of biocrude). For optimal excitation of the volume of fluid 105 including its materials, a frequency for the output sound waves should be selected (e.g., by the controller 160) that is near, substantially identical to, or identical to one of the eigenfrequencies of the volume of fluid 105 and/or the materials within the volume of fluid 105 (with or without boundary). Selecting a frequency for the sound wave that is near one of these eigenfrequencies may be used to improve the efficiency of various processes (e.g., mixing, stimulation, separation, or some combination thereof) related to manipulation of the volume of fluid 105 and any materials within the volume of fluid 105. More specifically, selecting the output frequency to be near (e.g., within a predetermined number of hertz/megahertz) one of these eigenfrequencies may be used to improve the efficiency the production of algal biocrude, including mixing the algae with the fluid 105, stimulation of the algae and/or the fluid 105, separation/harvesting/"dewatering" the algae from the fluid 105, or some combination thereof.

The dashed line 420 tracks admittance of the acoustic resonator with the fluid chamber 100 filled with volume of fluid 105. The admittance illustrated in dashed line 420 is clearly influenced both by the eigenfrequencies of both the volume of fluid 105 (i.e., shown in circles 410) and the at least part of the acoustic resonator device itself (i.e., shown in solid line 430) along the boundaries of the volume of fluid 105.

In other example embodiments, the controller 160 can select a frequency that is both near an eigenfrequency of the volume of fluid 105 (and/or its boundaries) and near an eigenfrequency of the empty acoustic resonator. One example may be the fluid eigenfrequency of FIG. 4 that is illustrated as having a frequency between 2.1 Mhz and 2.2 Mhz.

In other example embodiments, the controller 160 can function to balance algal harvesting efficiency while simultaneously avoiding energy loss. In such an example embodiment, the controller 160 can select a frequency that is both near an eigenfrequency of the volume of fluid 105 and away from an eigenfrequency of the empty acoustic resonator. One example may be the fluid eigenfrequency of FIG. 4 that is illustrated as having a frequency between 1.6 Mhz and 1.7 Mhz.

The resonance of the entire system, including the eigenfrequencies of the volume of fluid 105, may change over time depending on changing temperatures, pressures, and other properties within the fluid chamber 100. Thus, selecting a frequency for the sound waves that are to be emitted from the transducer 130 is not a trivial task, as it may require that the eigenfrequencies be tracked over time.

A user or controller 160 (or some combination thereof) may select a tracking frequency $f_m$ that corresponds to an eigenfrequency of the volume of fluid 105 (and/or its boundary conditions) and optionally that is either near or away from a previously-measured eigenfrequency of at least a subset of the empty acoustic resonator device (i.e., the transducer 130, the carrier 125, the reflector 120, the adhesive 165, the electrode A 140, the electrode B 145, the empty fluid chamber 100, the controller 160, the sensor 135, or some combination thereof.

The controller 160 may track the resonant peak $f_m$ over time, by injecting a low power signal and using transducer 130, sensor 130 or some combination thereof, using a phase lock loop and a zero I,V phase criteria, peak power tracking, or any other method.

The controller 160 may apply power to the system via a voltage source at a frequency: $f_0 = f_m(M/N) + f_{dc}$, where $f_0$ is an optimally selected peak, maximizing the energy efficiency factor (EEF), expected to be near the eigenfrequency of the empty acoustic resonator system (e.g., PZT and glass). M and N are integers, and $f_{dc}$ is a frequency and temperature dependent term to correct for acoustic dispersion. The quality factor (Q) is defined as the ratio of the frequency at the peak over the width of the peak. As used herein, EEF is proportional to the product of the frequency (in Hz) and the dimensionless quality factor (Q), or alternatively as the product of the frequency (in Hz) and the ratio of the stored energy in the system to the dissipated energy in the system. Tracking can be phase locked, but is not required to be.

Figure 5:
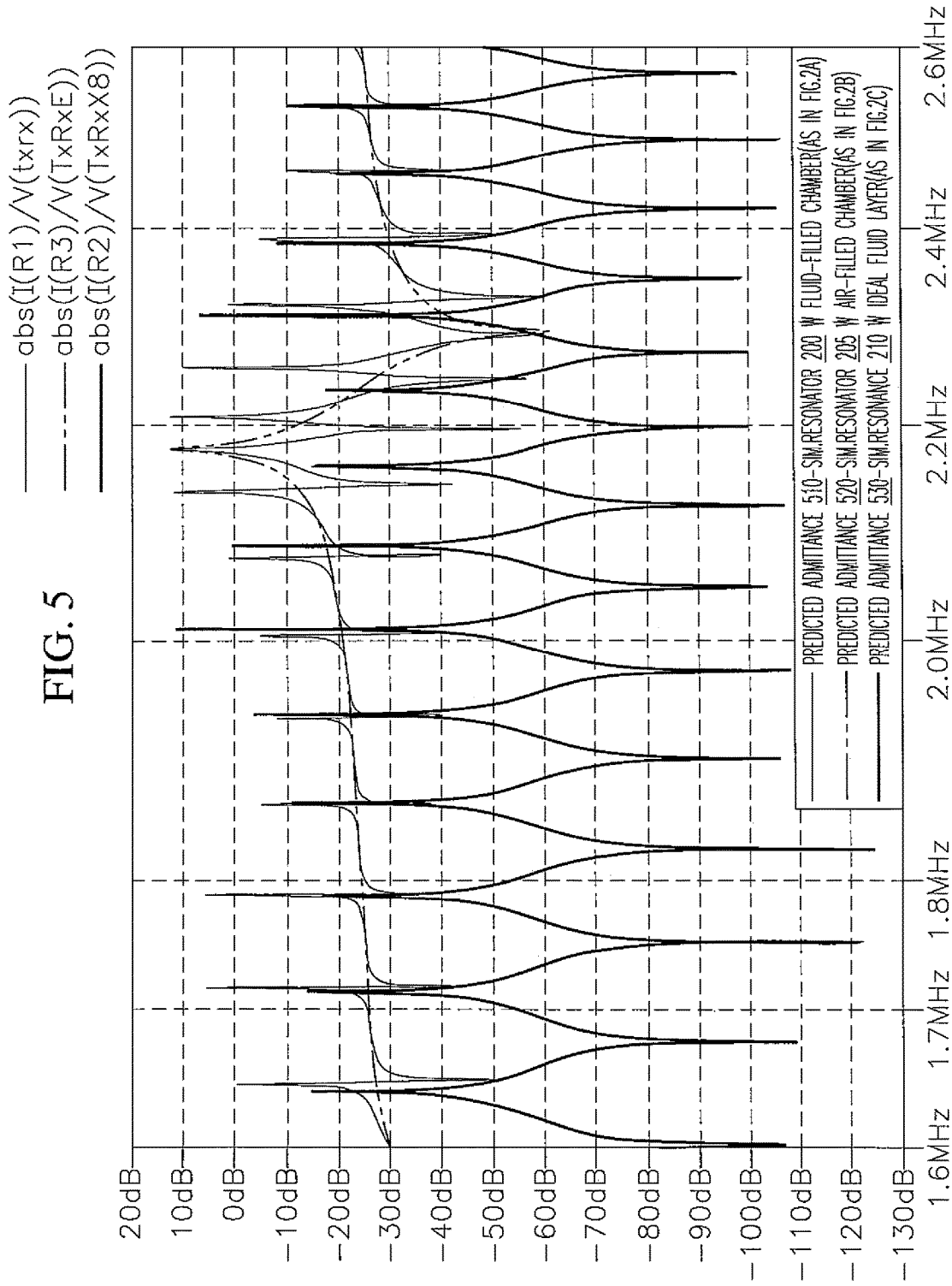
FIG. 5 is a graph charting admittance against frequencies (measured in megahertz) for the simulated acoustic resonator devices with transducers but no sensors of FIG. 2A and FIG. 2B against the ideal fluid layer resonance simulation of FIG. 2C.

FIG. 5 is a graph charting admittance against frequencies (measured in megahertz) for the simulated acoustic resonator devices with transducers but no sensors of FIG. 2A and FIG. 2B against the ideal fluid layer resonance simulation of FIG. 2C.

The graph of FIG. 5 is similar to the graph of FIG. 4 but entirely generated using the simulated acoustic resonator 200 of FIG. 2A (with volume of fluid 105) and the simulated acoustic resonator 205 of FIG. 2B (with air 230 in place of fluid 105) as compared to the ideal fluid layer resonance simulation 210 of FIG. 2C.

From the black line 530 of FIG. 5 that characterizes the ideal fluid layer resonance simulation 210 of FIG. 2C, it appears that a suitable frequency for an acoustic resonator to use may be just over 2.0 Mhz, since that appears to be the most prominent eigenfrequency of the volume of fluid 105 (and/or its boundary conditions) of those visible from the charted simulations. Because the system is not resonant at the fluid resonance just over 2.0 Mhz, the fluid layer resonant peak $f_0$ could be tracked by using a lower frequency resonance, $f_m$ peak just under 1.8 MHz, where the fluid layer resonance and the system resonance match.

Figure 6:
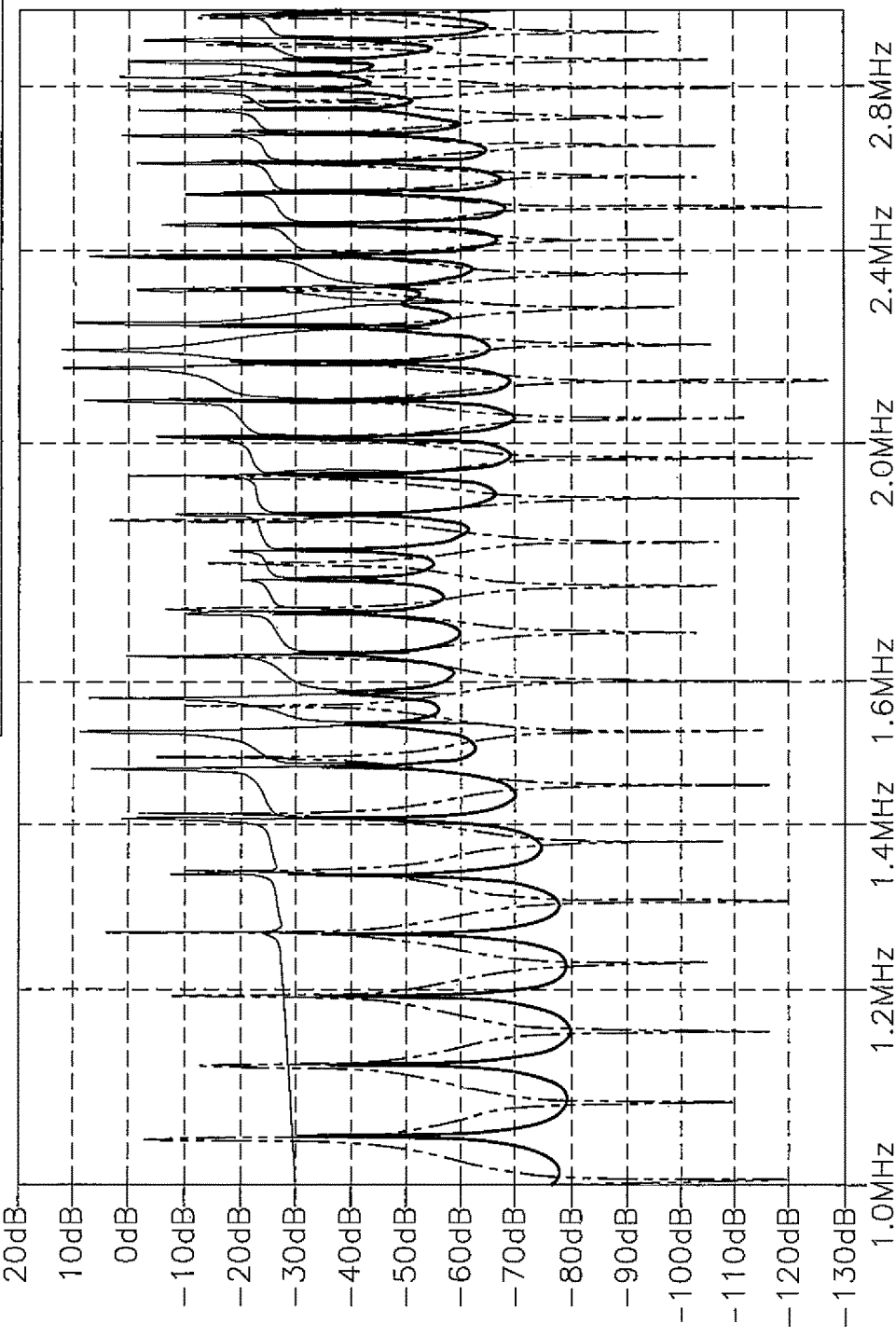
FIG. 6 is a graph charting admittance against frequencies (measured in megahertz) for the simulated acoustic resonator device with a transducer and a sensor of FIG. 3A against the ideal fluid layer resonance simulation of FIG. 3B.

FIG. 6 is a graph charting admittance against frequencies (measured in megahertz) for the simulated acoustic resonator device with a transducer and a sensor of FIG. 3A against the ideal fluid layer resonance simulation of FIG. 3B.

As noted in the discussion of FIG. 4, the predicted sensor output 630 of FIG. 6, whose output is illustrated as black line 630, tracks the predicted admittance 610 within the entirety of the simulated acoustic resonator 300 of FIG. 3A as illustrated in the light grey line 610. These both align with the simulated resonance 310 of the ideal fluid layer (of FIG. 3B) best when the frequency is far away from an eigenfrequency of the empty acoustic resonator (i.e., an eigenfrequency of the transducer 130, carrier 125, reflector 120, adhesive 165, electrodes 140/145, controller 160, sensor 135, or some combination thereof). By tracking fluid layer resonance across a narrow frequency range the fluid layer resonance across all frequencies can be estimated using the equation $f_0=f_m(M/N)+f_{dc}$ as described above in relation to FIG. 4.

FIG. 7 illustrates an exemplary computing system 700 that may be used to implement an embodiment of the present invention. For example, any of the computer systems or computerized devices described herein may, in at least some cases, be a computing system 700. The computing system 700 of FIG. 7 includes one or more processors 710 and memory 710. Main memory 710 stores, in part, instructions and data for execution by processor 710. Main memory 710 can store the executable code when in operation. The system 700 of FIG. 7 further includes a mass storage device 730, portable storage medium drive(s) 740, output devices 750, user input devices 760, a graphics display 770, and peripheral devices 780.

The components shown in FIG. 7 are depicted as being connected via a single bus 790. However, the components may be connected through one or more data transport means. For example, processor unit 710 and main memory 710 may be connected via a local microprocessor bus, and the mass storage device 730, peripheral device(s) 780, portable storage device 740, and display system 770 may be connected via one or more input/output (I/O) buses.

Mass storage device 730, which may be implemented with a magnetic disk drive or an optical disk drive, is a non-volatile storage device for storing data and instructions for use by processor unit 710. Mass storage device 730 can store the system software for implementing embodiments of the present invention for purposes of loading that software into main memory 710.

Portable storage device 740 operates in conjunction with a portable non-volatile storage medium, such as a floppy disk, compact disk or Digital video disc, to input and output data and code to and from the computer system 700 of FIG. 7. The system software for implementing embodiments of the present invention may be stored on such a portable medium and input to the computer system 700 via the portable storage device 740.

Input devices 760 provide a portion of a user interface. Input devices 760 may include an alpha-numeric keypad, such as a keyboard, for inputting alpha-numeric and other information, or a pointing device, such as a mouse, a trackball, stylus, or cursor direction keys. Additionally, the system 700 as shown in FIG. 7 includes output devices 750. Examples of suitable output devices include speakers, printers, network interfaces, and monitors.

Display system 770 may include a liquid crystal display (LCD), a plasma display, an organic light-emitting diode (OLED) display, an electronic ink display, a projector-based display, a holographic display, or another suitable display device. Display system 770 receives textual and graphical information, and processes the information for output to the display device. The display system 770 may include multiple-touch touchscreen input capabilities, such as capacitive touch detection, resistive touch detection, surface acoustic wave touch detection, or infrared touch detection. Such touchscreen input capabilities may or may not allow for variable pressure or force detection.

Peripherals 780 may include any type of computer support device to add additional functionality to the computer system. For example, peripheral device(s) 780 may include a modem or a router.

The components contained in the computer system 700 of FIG. 7 are those typically found in computer systems that may be suitable for use with embodiments of the present invention and are intended to represent a broad category of such computer components that are well known in the art. Thus, the computer system 700 of FIG. 7 can be a personal computer, a hand held computing device, a telephone ("smart" or otherwise), a mobile computing device, a workstation, a server (on a server rack or otherwise), a minicomputer, a mainframe computer, a tablet computing device, a wearable device (such as a watch, a ring, a pair of glasses, or another type of jewelry/clothing/accessory), a video game console (portable or otherwise), an e-book reader, a media player device (portable or otherwise), a vehicle-based computer, some combination thereof, or any other computing device. The computer system 700 may in some cases be a virtual computer system executed by another computer system. The computer can also include different bus configurations, networked platforms, multi-processor platforms, etc. Various operating systems can be used including Unix, Linux, Windows, Macintosh OS, Palm OS, Android, iOS, and other suitable operating systems.

In some cases, the computer system 700 may be part of a multi-computer system that uses multiple computer systems 700 (e.g., for one or more specific tasks or purposes). For example, the multi-computer system may include multiple computer systems 400 communicatively coupled together via one or more private networks (e.g., at least one LAN, WLAN, MAN, or WAN), or may include multiple computer systems 700 communicatively coupled together via the Internet (e.g., a "distributed" system), or some combination thereof.

Figure 8A:
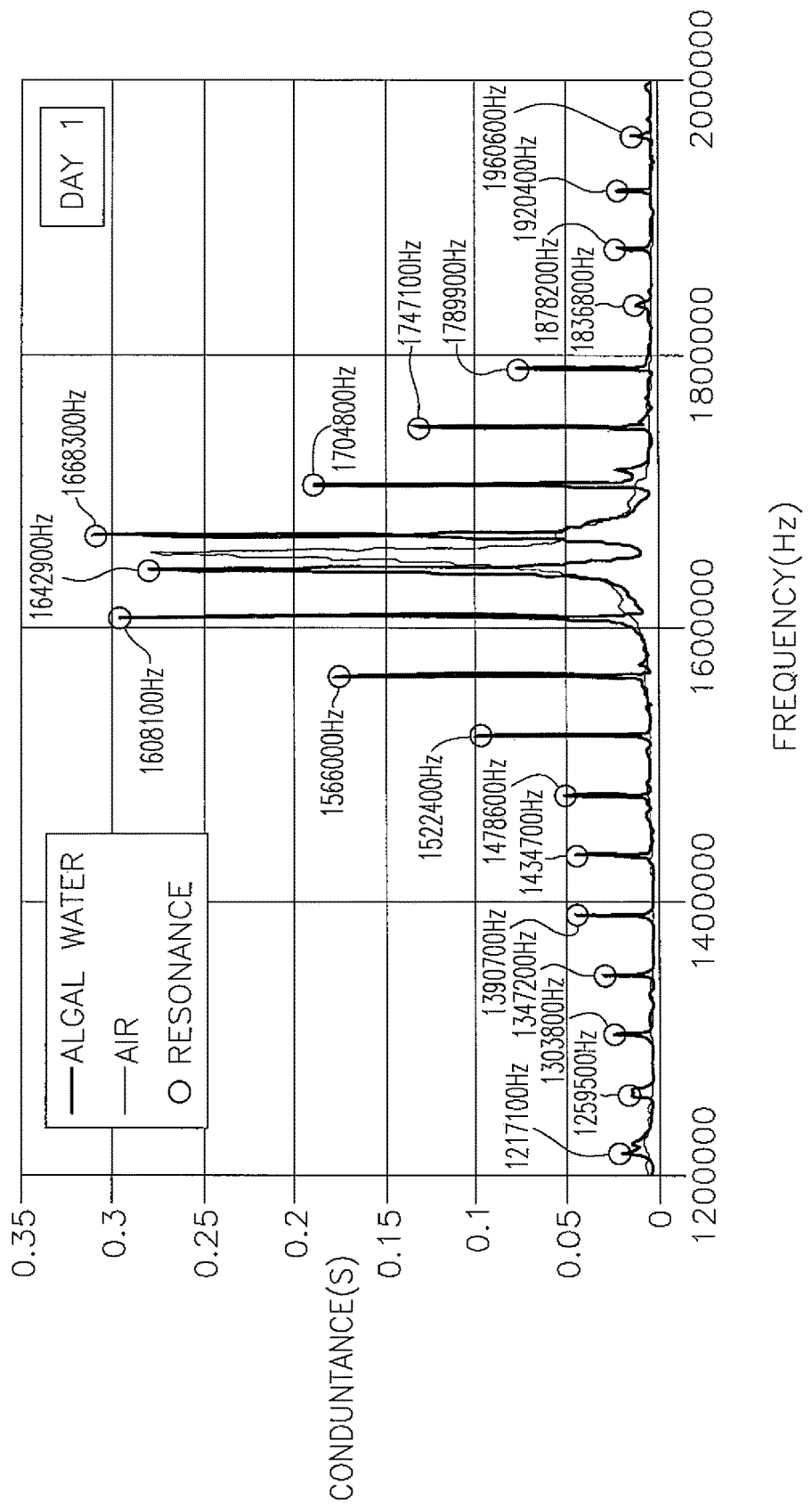
FIG. 8A is a graph charting conductance (measured in siemens) against frequencies (measured in Hertz) for an example acoustic resonator device.
Figure 8B:
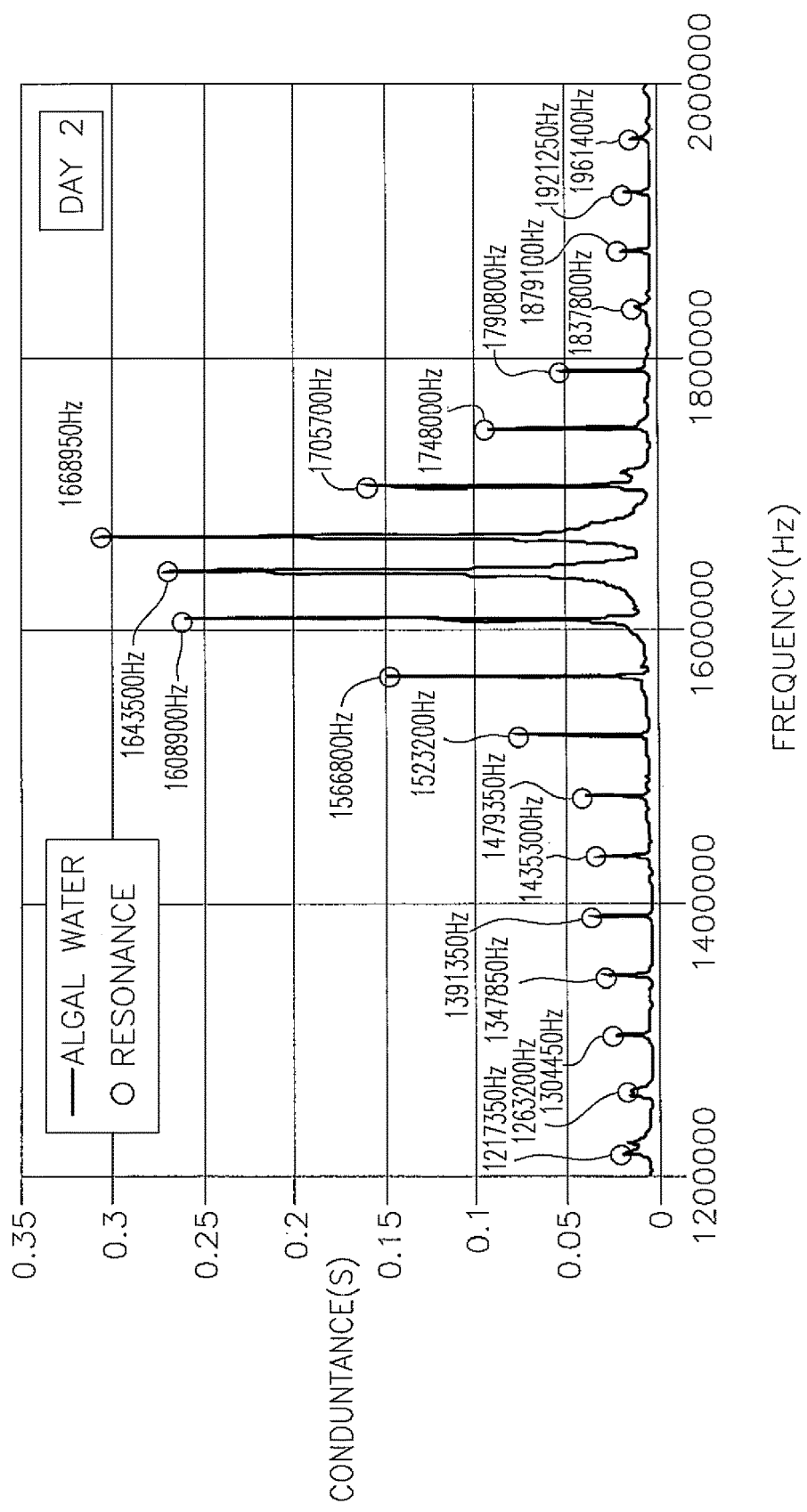
FIG. 8B is a graph charting conductance of the example resonator device of FIG. 7A after a predetermined time lapse.

An example acoustic resonator system was developed and tested. FIGS. 8A and 8B are graphs charting conductance (measured in siemens) against frequencies (measured in hertz) for the example acoustic resonator device with a transducer. FIG. 8A is a graph showing the conductance of the vessel filled with air (i.e., the grey curve) and filled with algae-containing water (i.e., the black curve). The circles in FIG. 8A identify the device resonance frequencies associated with each resonance peak when the device contains algal water.

FIG. 8B is a graph showing the conductance of the same vessel as FIG. 8A filled with algae-containing water (i.e., the black curve). The circles in FIG. 8B identify the device resonance frequencies associated with each resonance peak when the device contains algal water, which are slightly shifted in comparison to the resonance frequencies charted in FIG. 8A.

Figure 8C:
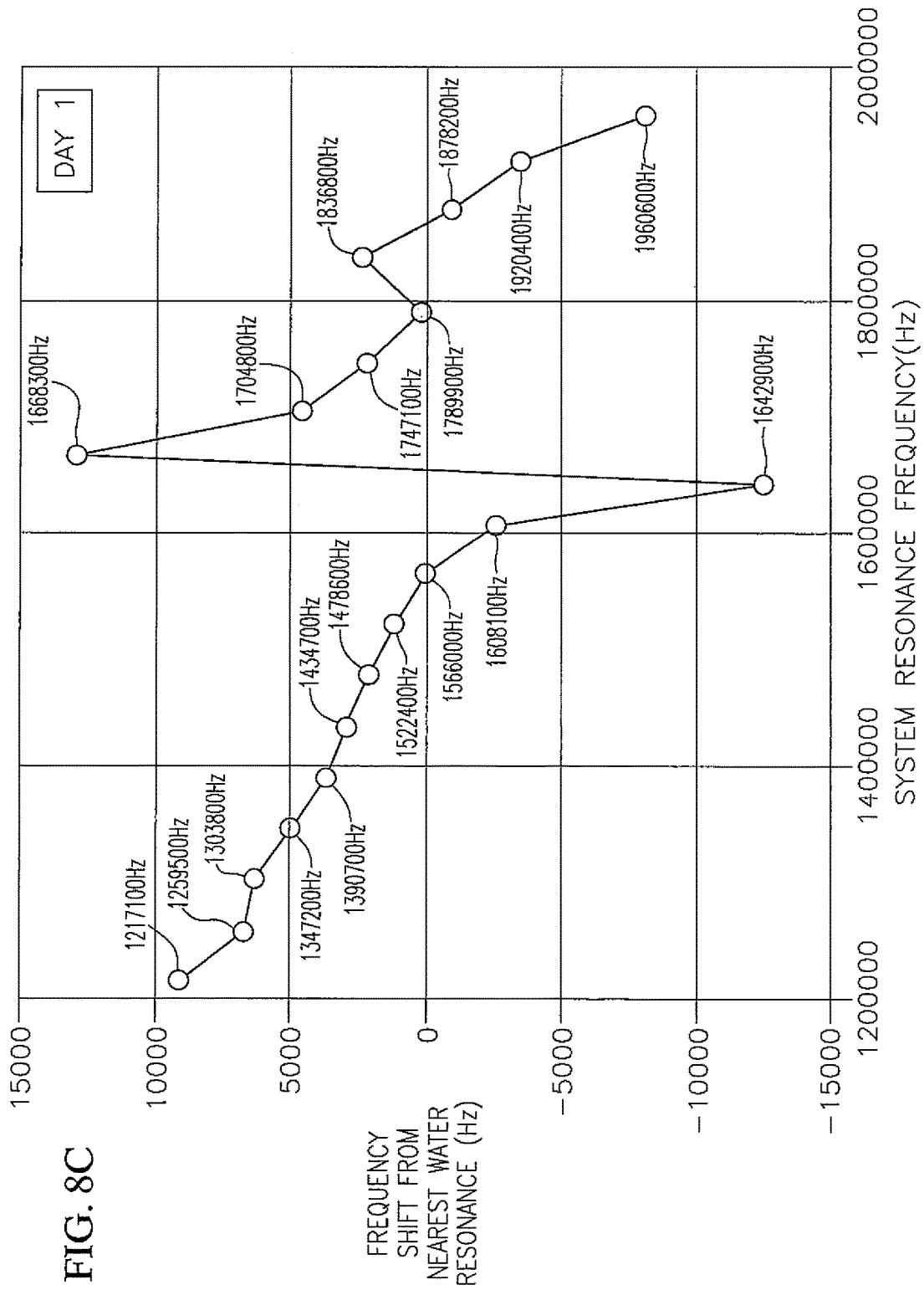
FIG. 8C is a graph charting the difference between an exemplary device resonance frequency and a nearest calculated algal water resonance frequency.

FIG. 8C is a graph charting the frequency difference between a given device resonance frequency and the nearest calculated algal water resonance frequency. As shown, at 1.56 MHz and 1.79 MHz, the algal water resonance frequency aligns with the device resonance frequency.

FIG. 8D is a graph charting the fraction of algae removed from the algal water when subjected to an acoustic standing wave when the device is operated at 1 Watt true power for a fixed time. FIG. 8D shows the amount of algae removed is correlated with the EEF. The EEF is measured by operating the transducer as an impedance sensor, and without knowledge of algae removal with the device. Each peak has an EEF, and is determined by the product of the peak resonance frequency and its quality factor (Q). The quality factor is measured as the ratio of the frequency at the peak to the peak width. The EEF values of each peak in FIGS. 8A and 8B are also listed. This example configuration is illustrative of the utility of the EEF in selecting an operating condition for efficient operation of the device.

While various flow diagrams provided and described above may show a particular order of operations performed by certain embodiments of the invention, it should be understood that such order is exemplary (e.g., alternative embodiments can perform the operations in a different order, combine certain operations, overlap certain operations, etc.).

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the following claims.

What is claimed is:

1. A system for acoustic fluid manipulation, the system comprising:
    an acoustic resonator device comprising:
        a fluid chamber that receives a volume of a fluid, the volume of the fluid including a phase-separate material, wherein one or more eigenfrequencies characterize at least the volume of the fluid;
        a carrier surface forming at least a first sidewall portion of the fluid chamber;
        a reflector surface forming at least a second sidewall portion of the fluid chamber; and
        a transducer coupled to the carrier surface, wherein receipt of electricity at the transducer from a voltage source triggers emission of an acoustic output by the transducer, the acoustic output thereby passing through the carrier surface and the fluid chamber toward the reflector surface, the transmission of the acoustic wave thereby exciting at least the volume of the fluid; and
    a controller configured to track the one or more eigenfrequencies over time in response to changes in one or more properties of the volume of the fluid and adjust the output frequency of the acoustic output by the transducer based on the one or more tracked eigenfrequencies,
    wherein the controller is configured to adjust the output frequency toward a frequency that is near one of the one or more tracked eigenfrequencies and away from an eigenfrequency of the acoustic resonator device when the acoustic resonator device is empty.

2. The system of claim 1, wherein the transducer comprises one of lead zirconate titanate (PZT) or a piezoelectric ceramic with one or more properties characteristic of lead zirconate titanate (PZT).

3. The system of claim 1, further comprising a sensor that tracks changes in the one or more eigenfrequencies.

4. The system of claim 1, wherein the output frequency is an ultrasonic frequency.

5. The system of claim 1, wherein the volume of fluid includes at least one of a gas, a liquid, or some combination thereof.

6. The system of claim 1, wherein the controller is configured to receive tracking data from the transducer and control the output frequency of the acoustic output to substantially match the output frequency to the one or more eigenfrequencies.

7. The system of claim 3, wherein the controller is configured to receive tracking data from the sensor and control the output frequency of the acoustic output to substantially match the output frequency to the one or more eigenfrequencies.

8. The system of claim 6, wherein the output frequency is selected to maximize the energy efficiency factor.

9. The system of claim 7, wherein the output frequency is selected to maximize the energy efficiency factor.

10. The system of claim 1, wherein the phase-separate material comprises algae.

11. A system for acoustic fluid manipulation, the system comprising:
    an acoustic resonator device comprising:
        a fluid chamber that receives a volume of a fluid, the volume of the fluid including a phase-separate material, wherein one or more eigenfrequencies characterize at least the volume of the fluid; and
        a transducer coupled to the fluid chamber to generate an acoustic output directed at the volume of fluid, the transmission of the acoustic wave thereby exciting at least the volume of the fluid; and
    a controller configured to track the one or more eigenfrequencies over time in response to changes in one or more properties of the volume of the fluid and adjust the output frequency of the acoustic output by the transducer based on the one or more tracked eigenfrequencies, wherein the controller is configured to adjust the output frequency toward a frequency that is near one of the one or more tracked eigenfrequencies and away from an eigenfrequency of the acoustic resonator device when the acoustic resonator device is empty.

12. The system of claim 11, further comprising a sensor that tracks changes in the one or more eigenfrequencies.

* * * * *